United States Patent
Kerman

(10) Patent No.: US 11,039,791 B2
(45) Date of Patent: Jun. 22, 2021

(54) LOCAL SIGNAL-TO-NOISE PEAK DETECTION

(71) Applicant: OWLET BABY CARE, INC., Lehi, UT (US)

(72) Inventor: Sean Kerman, Provo, UT (US)

(73) Assignee: Owlet Baby Care, Inc., Lehi, UT (US)

( * ) Notice: Subject to any disclaimer, the term of this patent is extended or adjusted under 35 U.S.C. 154(b) by 401 days.

(21) Appl. No.: 15/613,935

(22) Filed: Jun. 5, 2017

(65) Prior Publication Data

US 2017/0354381 A1 Dec. 14, 2017

Related U.S. Application Data

(60) Provisional application No. 62/348,057, filed on Jun. 9, 2016.

(51) Int. Cl.
*A61B 5/00* (2006.01)
*A61B 5/024* (2006.01)
*G16H 10/60* (2018.01)
*G16H 30/20* (2018.01)

(52) U.S. Cl.
CPC ........ *A61B 5/7203* (2013.01); *A61B 5/02416* (2013.01); *A61B 5/7221* (2013.01); *G16H 10/60* (2018.01); *G16H 30/20* (2018.01)

(58) Field of Classification Search
CPC . A61B 5/7203; A61B 5/7221; A61B 5/02416; G16H 10/60
See application file for complete search history.

(56) References Cited

U.S. PATENT DOCUMENTS

| 2014/0073960 | A1* | 3/2014 | Rodriguez-Llorente ..... A61B 5/7246 600/479 |
| 2015/0032447 | A1* | 1/2015 | Gunawan ................ G10L 25/84 704/233 |
| 2016/0051158 | A1* | 2/2016 | Silva .................. A61B 5/02416 600/479 |
| 2016/0361021 | A1* | 12/2016 | Salehizadeh ......... A61B 5/0245 |

OTHER PUBLICATIONS

Dubey et al, "Harmonic Sun-based Method for Heart Rate Estimation using PPG Signals Affected with Motion Artifacts", 2016. (Year: 2016).*

* cited by examiner

*Primary Examiner* — Regis J Betsch
*Assistant Examiner* — Jeremy A Delozier
(74) *Attorney, Agent, or Firm* — Workman Nydegger

(57) ABSTRACT

Biometric sensor systems are provided for identifying fundamental heart rate harmonics within noisy sensor signals. The system calculates a local signal-to-noise ratio for one or more identified frequency bands received in a biometric signal. The identified frequency bands are ranked based upon the calculated local signal-to-noise ratio. The fundamental heart rate is identified based upon the ranking of the identified frequency bands.

6 Claims, 3 Drawing Sheets

LOCAL SIGNAL-TO-NOISE PEAK DETECTION

CROSS-REFERENCE TO RELATED APPLICATIONS

This application claims priority to and the benefit of U.S. Provisional Application Ser. No. 62/348,057 entitled "LOCAL SIGNAL-TO-NOISE PEAK DETECTION", filed on Jun. 9, 2016, the entire contents of which is incorporated by reference herein in its entirety.

BACKGROUND

Computers and computing systems have affected nearly every aspect of modern living. Computers are generally involved in work, recreation, healthcare, transportation, entertainment, household management, etc.

As computer technology has increasingly become more compact and affordable, users have sought out ways to incorporate the technology into their daily lives. For example, smart phones and smart watches provide users with constant notifications, Internet access, and other related features. In conjunction with the widespread adoption of smart phones and smart watches, many users have also adopted various biometric tracking systems that are integrated within various digital devices, such as smart watches.

Many biometric trackers include the capability to monitor a user's heart rate and/or blood oxygen level. Conventional biometric tracking systems may utilize pulse oximetry technology to gather heart-rate and blood-oxygen data through the use of optical emitters and corresponding optical receivers. While professional-level pulse oximetry systems, such as those in hospitals, have been known and used for some time, mobile systems, such as those found in smart watches, are associated with various novel technical challenges.

For example, these mobile pulse oximetry systems are often battery-powered and as such must operate within a much more power constrained environment than professional-level pulse oximetry systems, which are typically powered through a power outlet. Similarly, mobile pulse oximetry systems are capable of being worn while a user goes about their normal daily activities. In contrast, hospital-based systems are predominately attached to patients who are lying in hospital beds. Data signals received throughout a user's daily activities typically include more noise and distortion than the signals received from users who are lying in hospital beds. Additionally, as mentioned above, mobile biometric tracking systems must process and analyze the receive signals using processors that are power constrained.

Accordingly, there are many technical challenges to overcome within mobile pulse oximetry systems. The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments disclosed herein include a system that computes a local signal-to-noise ratio for one or more identified peaks within a frequency-domain biometric signal. Based upon the computed local signal-to-noise ratio, the system ranks various frequency bands. The system identifies the best rated frequency band as the fundamental heart-rate within the signal.

Disclosed embodiments include a computer system for identifying fundamental heart rate harmonics within noisy sensor signals. The system includes one or more processors and one or more computer-readable media having stored thereon executable instructions that when executed by the one or more processors configure the computer system to perform various acts. For example, the system receives, at a sensor input interface, biometric signal data from a sensor in contact with a user.

The system then extracts, using a computer processor, a frequency-domain biometric signal from the biometric signal data. Using the frequency-domain biometric signal, the system identifies a candidate frequency band within the frequency-domain biometric signal. The system also identifies one or more harmonics associated with the candidate frequency band.

The system then generates a summed local signal value by summing an amplitude of the candidate frequency band with amplitudes of each of the one or more harmonics. Additionally, the system generates a summed local noise value by summing amplitudes associated with signals that occur between the one or more harmonics. Further, the system calculates a candidate figure of merit based upon the summed local signal value and the summed local noise value. The system then identifies a fundamental harmonic within the frequency-domain biometric signal based upon the candidate figure of merit.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Embodiments disclosed herein include methods, systems, and apparatuses that compute a local signal-to-noise ratio for one or more identified peaks within a frequency-domain biometric signal. Based upon the computed local signal-to-noise ratio, the system ranks various potential frequency bands. The system identifies the best rated frequency band as the fundamental heart-rate within the signal.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 1:
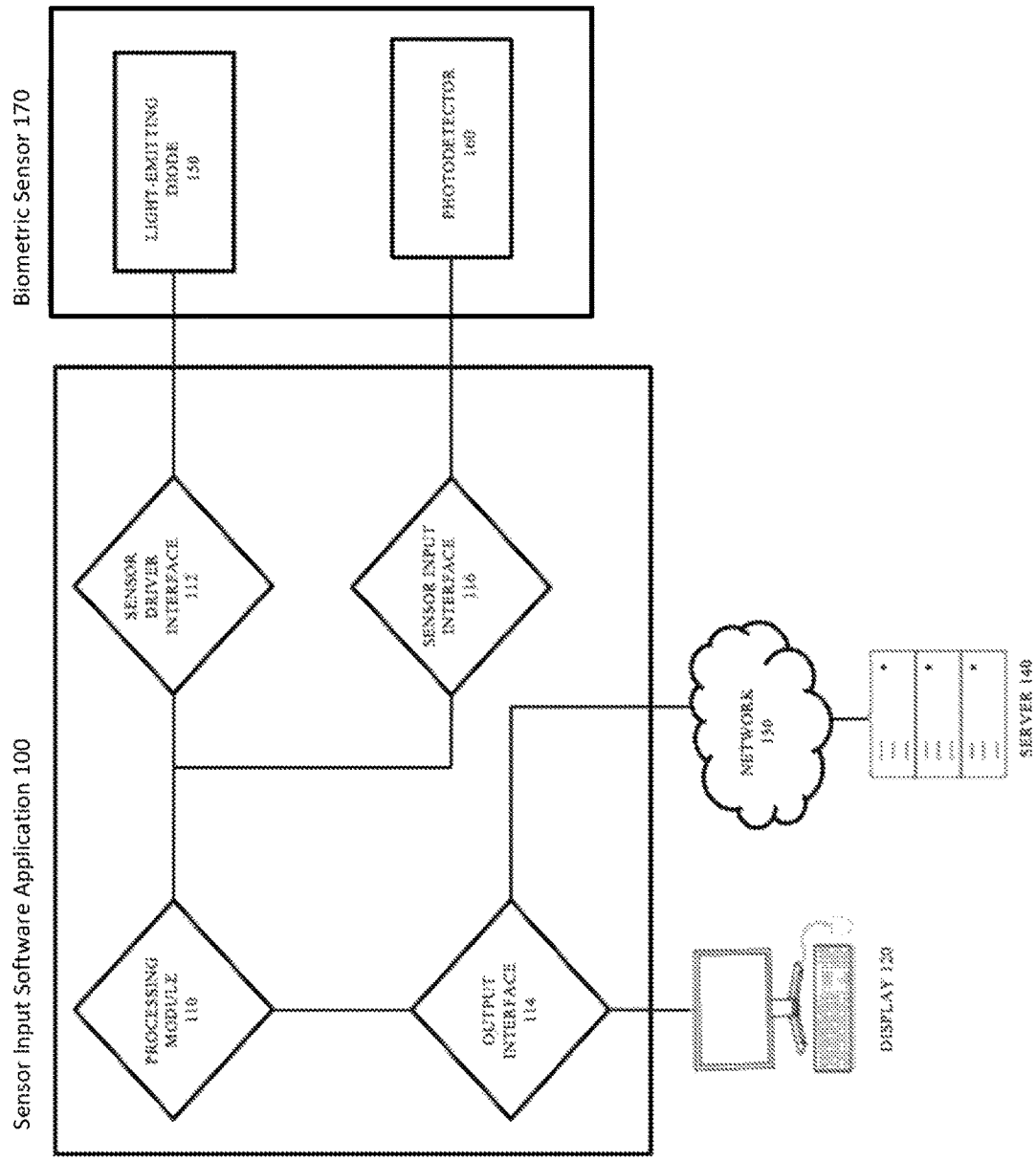
FIG. 1 illustrates an embodiment of a system for identifying fundamental heart rate harmonics within noisy sensor signals.

Embodiments disclosed herein include methods, systems, and apparatuses that identify biometric readings within noisy sensor signals. For example, disclosed embodiments compute a local signal-to-noise ratio for one or more identified peaks within a frequency-domain biometric signal. Based upon the computed local signal-to-noise ratio, the system rates various potential peaks. The system identifies the best rated peaks as the fundamental heart-rate within the signal Turning now to the figures, FIG. 1 depicts a sensor input software application 100 that comprises various depicted modules and components. For example, the sensor input software application 100 comprises a processing module 110, a sensor driver interface 112, a sensor input interface 116, and an output interface 114. One will understand, however, that the depicted modules and components are provided only for the sake of example and clarity and that in additional or alternative embodiments different combinations and descriptions of components and modules can be equivalently we used.

The sensor input software application 100 is configured to communicate to a biometric sensor 170, process received information, and provide the processed information to a user. In at least one embodiment, the processing module 110 communicates, to a sensor driver interface 112, instructions that cause the sensor driver interface 112 to activate a light-emitting diode 150. The sensor driver interface 112 may comprise a voltage controller, a current controller, or a conventional communications port, such as a USB interface, a serial interface, or any other known interface.

A photodetector 160 receives the emitted light, either directly through transmittance or indirectly through reflectance, after the light has interacted with the user's tissue. The photodetector 160 communicates gathered light data to a sensor input interface 116 within the sensor input software application 100. As used herein, the sensor input interface 116 may comprise a multi-meter or a conventional communications port, such as a USB interface, a serial interface, or any other known interface.

The processing module 110 processes the received light data using various methods that will be described more fully herein. For example, the processing module 110 identifies desirable information within the received flight data and excludes noise and distortion that would otherwise result in incorrect biometric readings. After processing the light data, the processing module 110 communicates the processed light data to the output interface 114. In various additional or alternative embodiments, the output interface 114 communicates with various external devices. For example, the output interface 114 communicates with a display 120 that is accessible to the user. Display 120 may comprise a smart phone display, a smart watch display, a standard computer display, an audio speaker, an actuator, or any other interface capable of providing information and/or notifications to the user.

Additionally, the output interface 114 can communicate information through a network 130 to a server 140. As used herein, the server 140 may be configured to store the receive information, process the received information, display the received information, or otherwise handle the received information. For example, in at least one of implementation, the processing module 110 only partially processes the received light data, and the server 140 completes the processing. As such, in at least one embodiment, the sensor input software application 100 may comprise a distributed system where portions of the sensor input software application 100 are executed on various different, and possibly geographically remote, computer systems. In contrast, in at least one embodiment, the sensor input software application 100 is executed wholly within a mobile computing device that is in direct communication with the light emitting diode 150 and the photodetector 160.

In any case, the sensor input software 100 of FIG. 1 is capable of receiving and processing biometric signals from a biometric sensor. In at least one embodiment, it is necessary to identify specific data from within a noisy biometric signal. For instance, when receiving a biometric signal from a pulse-oximeter, it may be desirable to identify a fundamental heart frequency within the noisy biometric signal. The fundamental heart frequency may be associated with the heart rate of a user. In a noisy biometric signal, however, there may exist multiple potential frequency-domain peaks scattered throughout the noise biometric signal. Some of the peaks may be wholly associated with noise; while other peaks may be associated with harmonics caused by the user's heartbeat. As such, the sensor input software 100 must distinguish between noise-induced peaks and harmonics. Accordingly, embodiments of the sensor input software 100 are capable of identifying a fundamental harmonic within a biometric signal, where the fundamental harmonic is associated with a user's heart rate.

Figure 2:
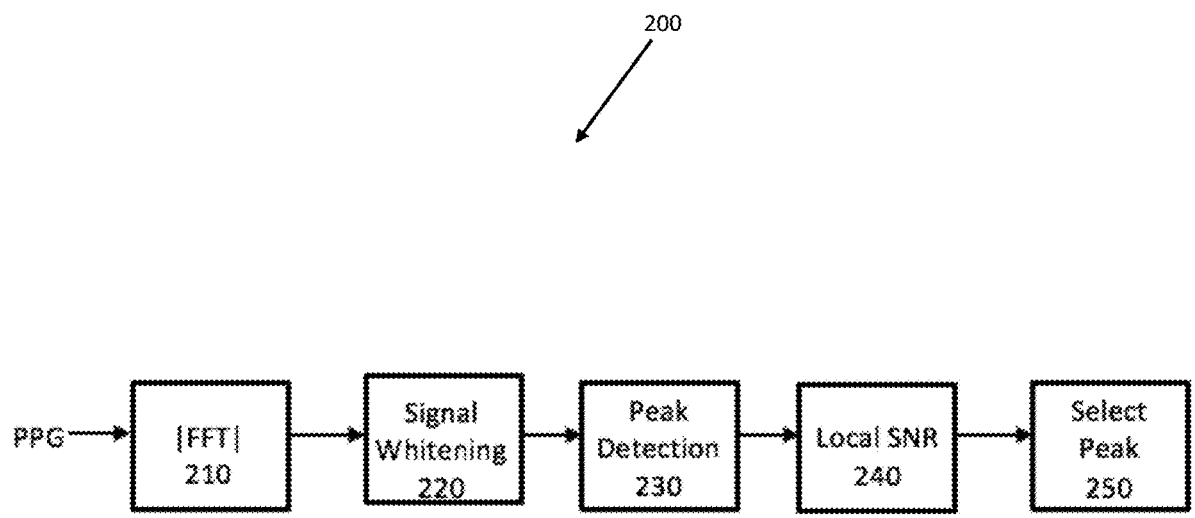
FIG. 2 illustrates an embodiment of a flow chart for identifying fundamental heart rate harmonics within noisy sensor signals.

For example, FIG. 2 illustrates an embodiment of a flow chart for method 200 of identifying fundamental heart rate harmonics within noisy sensor signals. In particular, FIG. 2 depicts a biometric signal, in this example a photoplethysmogram ("PPG"), being processed in a fast Fourier transform ("FFT") process 210. The resulting FFT signal is then processed through a signal whitening process 220 that applies some function F(n) to each bin within the resulting FFT signal. In at least one embodiment, the signal whitening process 220 comprises multiplying the magnitude of each bin within the resulting FFT signal by its bin index in order to give more weight to higher harmonics.

Following the signal whitening process 220, the whitened signal is processed through a peak detection process 230. Various different methods may be utilized to identify respective peaks within the whitened signal. As a non-limiting example, peaks may be identified by identifying a peak value within a set of adjacent bins. For example, any bin that is associated with a higher value than both of its respective adjacent bins may be designated as a peak.

Additionally, in at least one embodiment, the peak detection process 230 groups multiple adjacent bins into a frequency band. For instance, a particular signal may bleed into adjacent bins. As such, the signal detection process 230 groups adjacent bins together in association with a single signal based upon attributes of each grouped bin. For example, the signal detection process 230 may group a predefined number of bins together with each respective signal. Regardless of the method used to identify the signal, the signal detection process 230 identifies various peaks (i.e. potential fundamental harmonics) for processing.

Once various frequency bands are identified, the identified bands are provided to a local signal-to-noise ratio ("SNR") process 250. In at least one embodiment, the local SNR for each identified peak is computed by identifying the first M harmonics of each peak, where M is some integer (for example three). One of skill in the art will understand that there are several ways for harmonics to be identified. For example, as a non-limiting embodiment, the local SNR process 240 identifies the harmonics by identifying signal components that are one, two, three, etc. times the frequency of each respective frequency band (i.e., the proposed fundamental harmonic).

Once the harmonics are identified, the harmonic bins for each respective identified frequency band are all summed to form a total local signal value "S". The signal values between the first and harmonics that were not included as part of the signal S are then summed to compute a total local noise value "N" for each respective identified peak. In at least one embodiment, the local SNR process 240 also includes bins of a lower frequency than the proposed fundamental harmonic or higher frequency than the Mth harmonic in the noise calculation. For example, if the proposed fundamental harmonic (i.e., identified peak) is within bin n, then the local SNR process 240 includes bins down to n/2 within the total noise calculation. In at least one embodiment, including the bins down to n/2 bin within the total noise calculation assists in identifying if the n/2 bin is in fact the fundamental harmonic.

Once the total signal values and total noise values for each respective identified frequency bands are computed, they are normalized by dividing each by the number of respective bins summed. One will understand, this provides an average local signal value across each respective signal band and associated harmonic bins and an average local noise value across all intermediate bins between the respective peak and harmonic bins. The local SNR process 240 then computes the SNR for each identified peak by dividing the average local signal value by the average noise value associated with each identified peak. Once all proposed peaks have had a local SNR calculated, the proposed peaks are all ranked based upon local SNR values. The bin with the highest local SNR value is identified as the fundamental harmonic.

Figure 3:
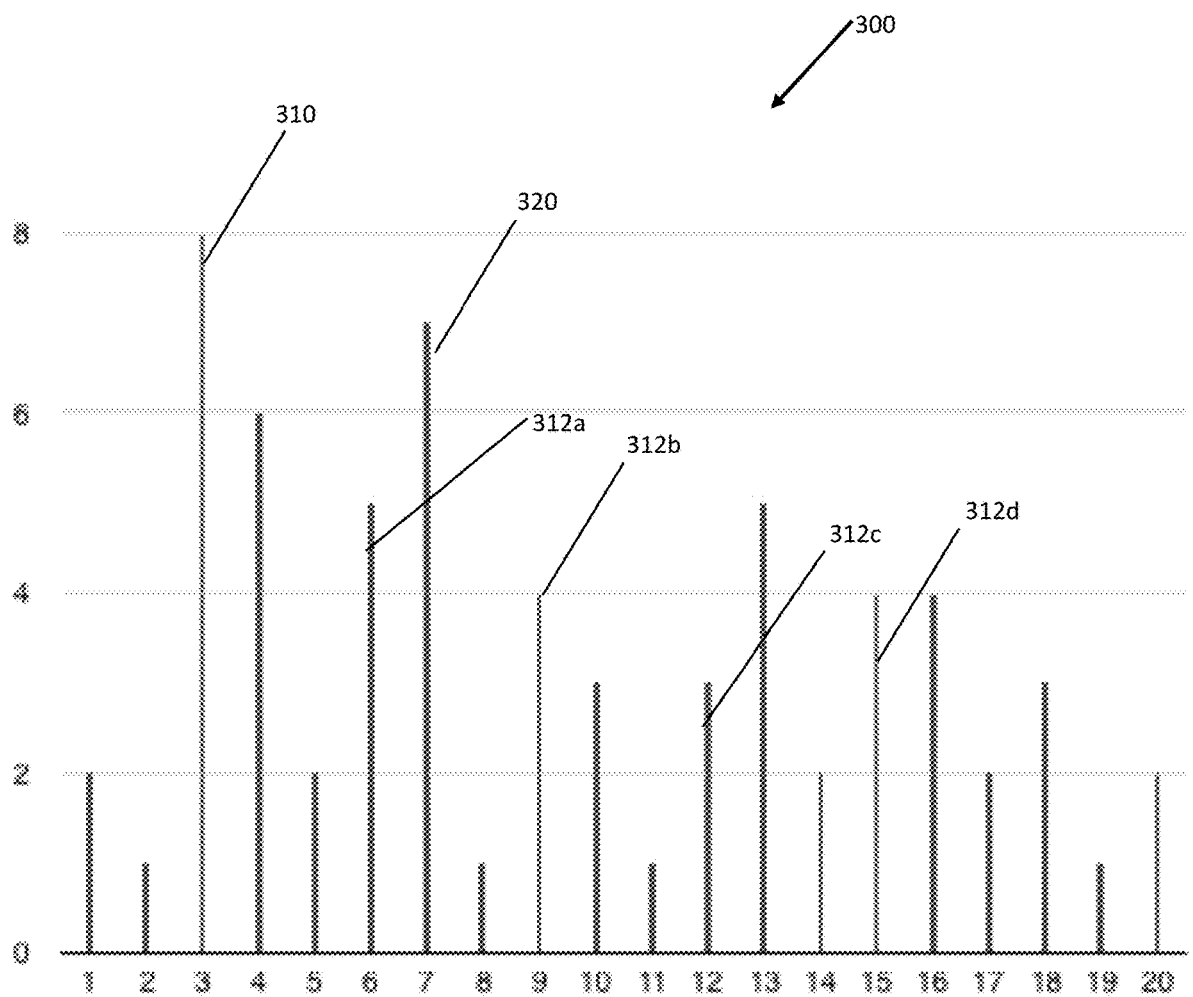
FIG. 3 illustrates an embodiment of a frequency-domain graph of a noisy biometric signal.

For example, FIG. 3 illustrates an embodiment of a frequency-domain graph of a noisy biometric signal 300. In particular, FIG. 3 depicts a discrete fast Fourier transform of an exemplary biometric signal. The depicted noisy biometric signal 300 comprises significant noise components. One will understand that the depicted noisy biometric signal 300 is merely provided for the sake of example and clarity and does not necessarily reflect a received biometric signal.

As explained above, the sensor input software application 100 can identify one or more candidate peaks within the frequency domain biometric signal 300. For example, the sensor input software application 100 may identify as potential peaks at least peak 310 and peak 320. Additionally, using the methods described above, the sensor input software application 100 identifies various harmonics associated with each frequency band. For instance, the sensor input software application 100 may identify harmonics 312a, 312b, 312c, and 312d as being associated with frequency band 310.

The sensor input software application 100 then calculates a total signal by summing the values of frequency band 310, first harmonic 312a, second harmonic 312b, third harmonic 312c, and fourth harmonic 312d. After calculating the total signal value, the sensor input software application 100 calculates an average total signal by dividing the previously calculated total signal by the number of bins associated with the frequency band and harmonics, or in this case by five.

The sensor input software application 100 then calculates a total noise by summing the signal values between peak 310 and the first harmonic 312a, and between each subsequent harmonic. The sensor input software application 100 divides the total noise by the number of bins utilized in calculating the total noise. Using the calculated information, the sensor input software application 100 calculates a figure of merit based upon the summed local signal value (e.g., the average local signal value) and the total noise value (e.g., the average local noise value). To calculate the figure of merit, in at least one embodiment, the sensor input software application 100 divides the average local signal value by the average local noise value.

The sensor input software application 100 then continues to perform the above calculations for each identified potential frequency band within the noisy biometric signal 300. For example, the sensor input software application 100 identifies potential harmonics that are associated with frequency band 320 and calculates a figure of merit for frequency band 320 using the above-described method. Once the sensor software application 100 calculates respective figures of merit for each identified frequency band, the sensor input software application 100 identifies a fundamental harmonic of the biometric signal based upon the respective frequency band with the highest candidate figure of merit.

Accordingly, in at least one embodiment, disclosed embodiments calculate a local signal-to-noise ratio for one or more identified frequency bands within a noisy biometric signal 300. The disclosed embodiments can identify a fundamental harmonic of the biometric signal based upon a ranking of the figures of merit for various identified peaks.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system for identifying fundamental heart rate harmonics within noisy sensor signals, comprising:
   one or more processors; and
   one or more computer-readable media having stored thereon executable instructions that when executed by the one or more processors configure the computer system to perform at least the following:
   receive, at a sensor input interface, biometric signal data from a sensor in contact with a user;
   extract, using a computer processor, a frequency-domain biometric signal from the biometric signal data;
   identify a candidate frequency band within the frequency-domain biometric signal;
   identify one or more harmonics associated with a candidate peak, wherein the one or more harmonics and the candidate peak are within the candidate frequency band;
   generate a summed local signal value by summing an amplitude of the candidate peak with amplitudes of each of the one or more harmonics;
   generate a summed local noise value by summing amplitudes associated with signals that occur between the one or more harmonics and dividing the summation of amplitudes by a number of bins utilized in the summation of amplitudes;
   calculate a candidate figure of merit by dividing the summed local signal value by the summed local noise value;
   identify a fundamental harmonic within the frequency-domain biometric signal based upon the candidate figure of merit; and
   display a user's heart rate based upon the identified fundamental harmonic.

2. The computer system of claim 1, wherein the biometric signal data comprises a photoplethysmogram.

3. The computer system of claim 1, wherein the biometric sensor data comprises a photodetector.

4. The computer system of claim 1, wherein the executable instructions include instructions that are executable to configure the computer system to:
   identify another frequency band within the frequency-domain biometric signal;
   identify one or more other harmonics associated with the other frequency band;
   generate another summed local signal value by summing an amplitude of the other frequency band with amplitudes of each of the one or more other harmonics;
   generate another summed local noise value by summing amplitudes associated with signals that occur between the one or more other harmonics;
   calculate another candidate figure of merit by dividing the other summed local signal value by the other summed local noise value;
   rank the candidate peak and the other peak based upon their respective figure of merit values; and identify the fundamental harmonic within the frequency-domain biometric signal by identifying a frequency band associated with the highest ranked figure of merit.

5. A method for identifying fundamental heart rate harmonics within a noisy photoplethysmogram, the method comprising:

receiving, at a sensor input interface, a noisy photoplethysmogram from a photodetector in contact with a user;

extracting, using a Fast-Fourier Transform, a frequency-domain biometric signal from the noisy photoplethysmogram;

identifying a first candidate frequency band within the frequency-domain biometric signal;

calculating a first candidate figure of merit by dividing a first summed local signal value by a first summed local noise value, wherein:

the first summed local signal value comprises a summation of an amplitude of a first candidate peak with amplitudes of each of one or more first harmonics of the first candidate frequency band, and a first summed local noise value comprises a summation of amplitudes associated with signals that occur between the one or more first harmonics divided a number of bins utilized in the summation of amplitudes;

identifying a second candidate frequency band within the frequency-domain biometric signal;

calculating a second candidate figure of merit by dividing a second summed local signal value by a second summed local noise value, wherein:

the second summed local signal value comprises a summation of an amplitude of a second candidate peak within the second candidate frequency band with amplitudes of each of one or more second harmonics of the second candidate frequency band, and a second summed local noise value comprises a summation of amplitudes associated with signals that occur between the one or more second harmonics;

ranking the first candidate frequency band and second candidate frequency band based upon the first candidate figure of merit and the second candidate figure of merit;

identifying a fundamental harmonic heartbeat associated with the user within the noisy photoplethysmogram based upon the ranking; and displaying the user's heart rate based upon the fundamental harmonic heartbeat associated with the user.

6. The method as recited in claim 5, wherein extracting the frequency-domain biometric signal from the noisy photoplethysmogram comprises generating the frequency-domain biometric signal within a plurality of bins.

* * * * *